US00PP14850P2

(12) United States Plant Patent
Brljevich et al.

(10) Patent No.: US PP14,850 P2
(45) Date of Patent: Jun. 1, 2004

(54) CALLA LILY PLANT NAMED 'TAHITI'

(50) Latin Name: *Zantedeschia sprengeri*
Varietal Denomination: Tahiti

(75) Inventors: Trevor Brljevich, Maungaturoto (NZ); Yvonne Brljevich, Maungaturoto (NZ)

(73) Assignee: Pukekaroro Exotics Ltd. (NZ)

( * ) Notice: Subject to any disclaimer, the term of this patent is extended or adjusted under 35 U.S.C. 154(b) by 0 days.

(21) Appl. No.: 10/638,666

(22) Filed: Aug. 11, 2003

(51) Int. Cl.[7] ..... A01H 5/00
(52) U.S. Cl. ..... Plt./263
(58) Field of Search ..... Plt./263

*Primary Examiner*—Kent Bell
(74) *Attorney, Agent, or Firm*—Webb Ziesenheim Logsdon Orkin & Hanson P.C.

(57) ABSTRACT

'Tahiti' is a new variety of calla lily having beautiful apricot-orange colored spathes.

3 Drawing Sheets

Botanical classification: *Zantedeschia sprengeri.*
Varietal denomination: 'Tahiti'.

BACKGROUND OF THE NEW PLANT

The present invention comprises a new and distinct cultivar of calla lily, botanically known as *Zantedeschia sprengeri* and hereinafter referred to by the cultivar name 'Tahiti'.

'Tahiti' was discovered in 1997 and chosen from a selection of seedling tubers of unknown parentage in Maungaturoto, New Zealand. The first act of asexual reproduction of 'Tahiti' by tissue culture was performed in 1998 in Auckland, New Zealand. Subsequent asexual reproductions by tissue culture have demonstrated that the combination of characteristics as herein disclosed for the new cultivar are retained through successive generations of asexual reproduction.

The following traits have been repeatedly observed and determined to be basic characteristics of 'Tahiti' which, in combination, distinguish this calla lily as a new and distinct cultivar:

1. 'Tahiti' has a different shaped leaf with fewer leaf maculations than 'Sunglow' (unpatented), 'Inspiration' (unpatented), and 'Tropica' (unpatented); and
2. 'Tahiti' is more apricot-orange colored than 'Neroli' (unpatented) and 'Passionfruit' (unpatented).

BRIEF DESCRIPTION OF THE DRAWINGS

The accompanying photographic drawings illustrate the new variety, with the colors being as nearly true as is possible with color illustrations of this type.

DESCRIPTION OF THE NEW PLANT

Figure 1:
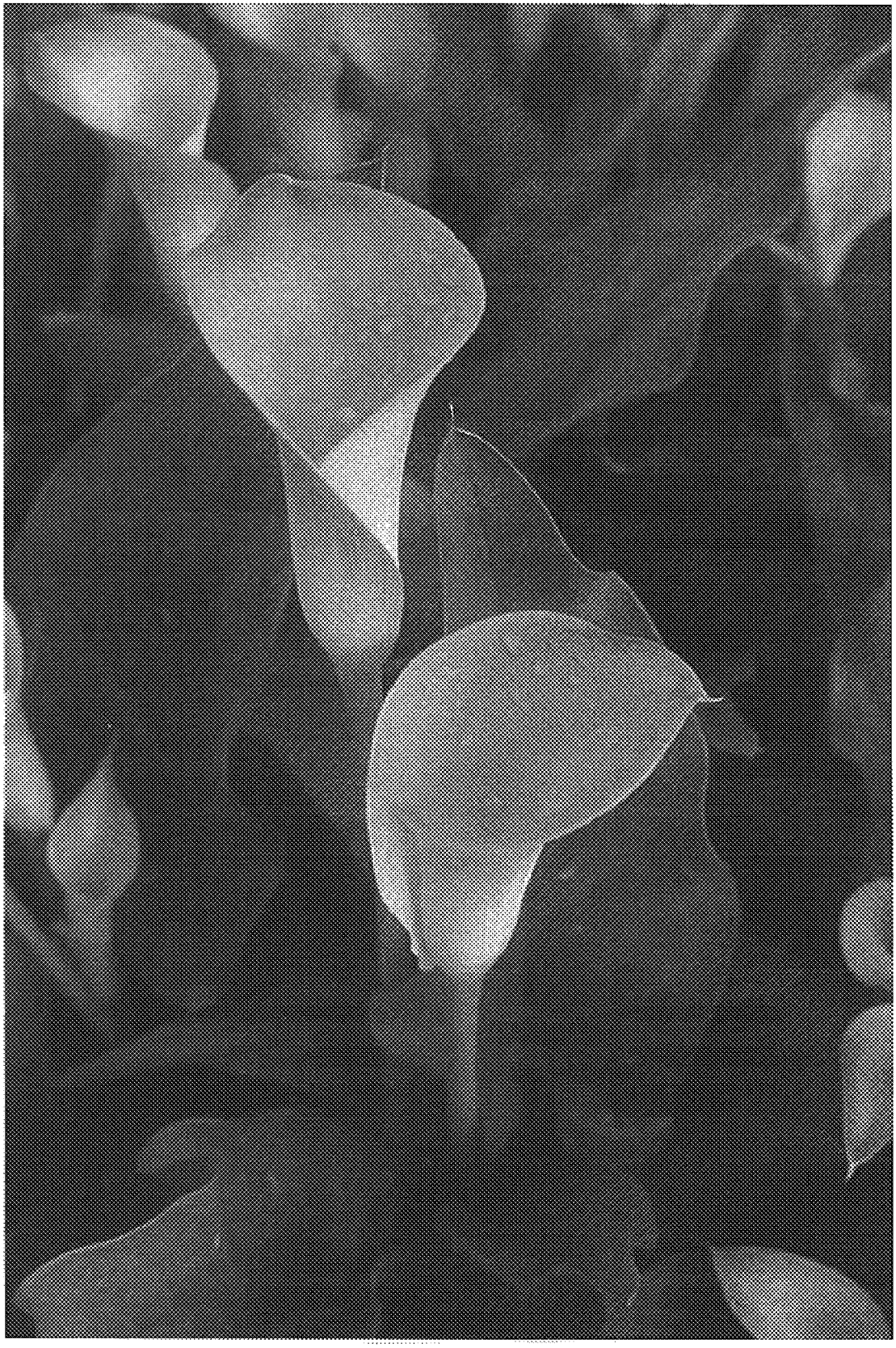
FIG. 1 is a close-up photograph of inflorescences of the new variety.
Figure 2:
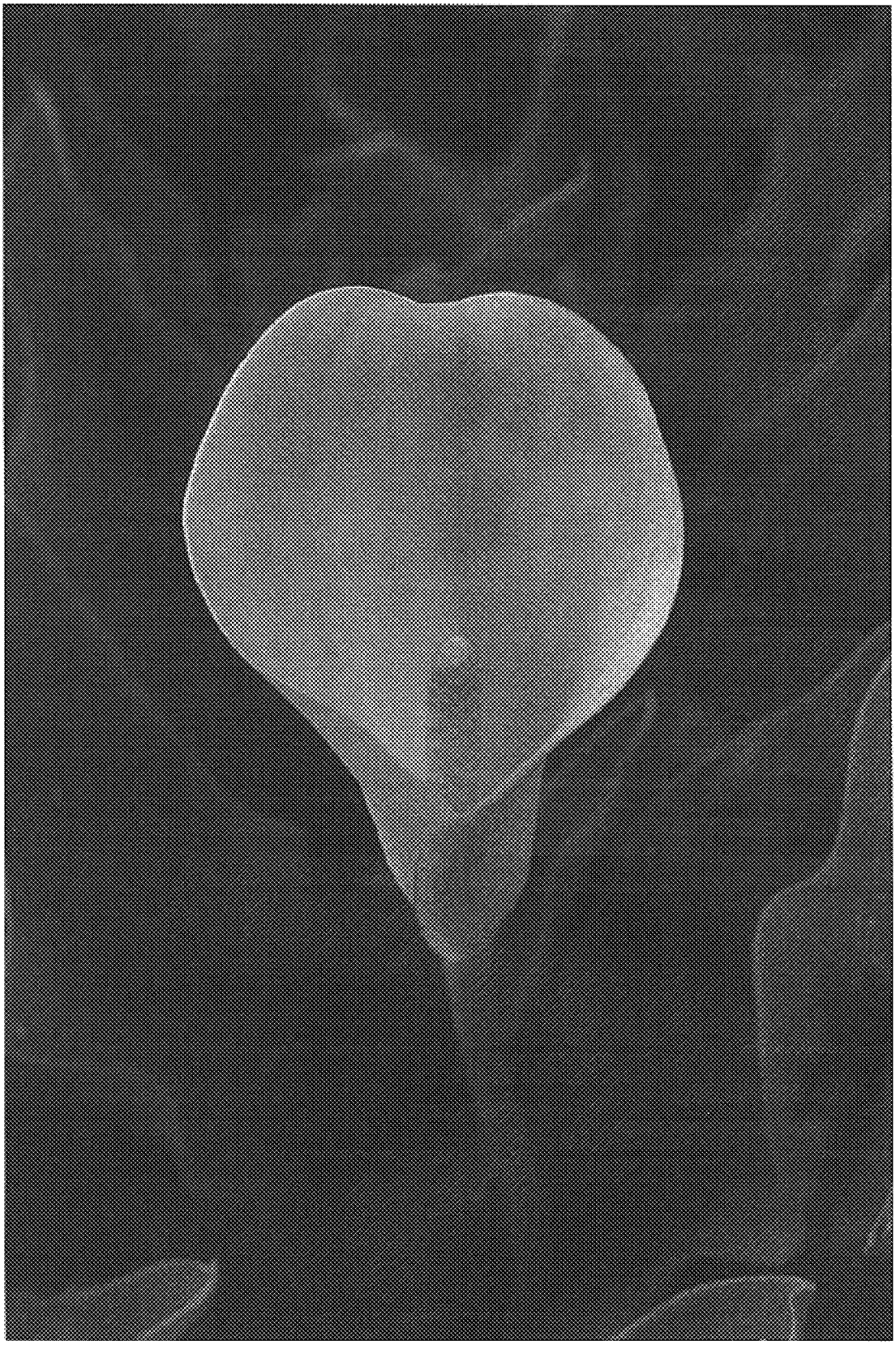
FIG. 2 is a close-up photograph of a single inflorescence of the new variety.
Figure 3:
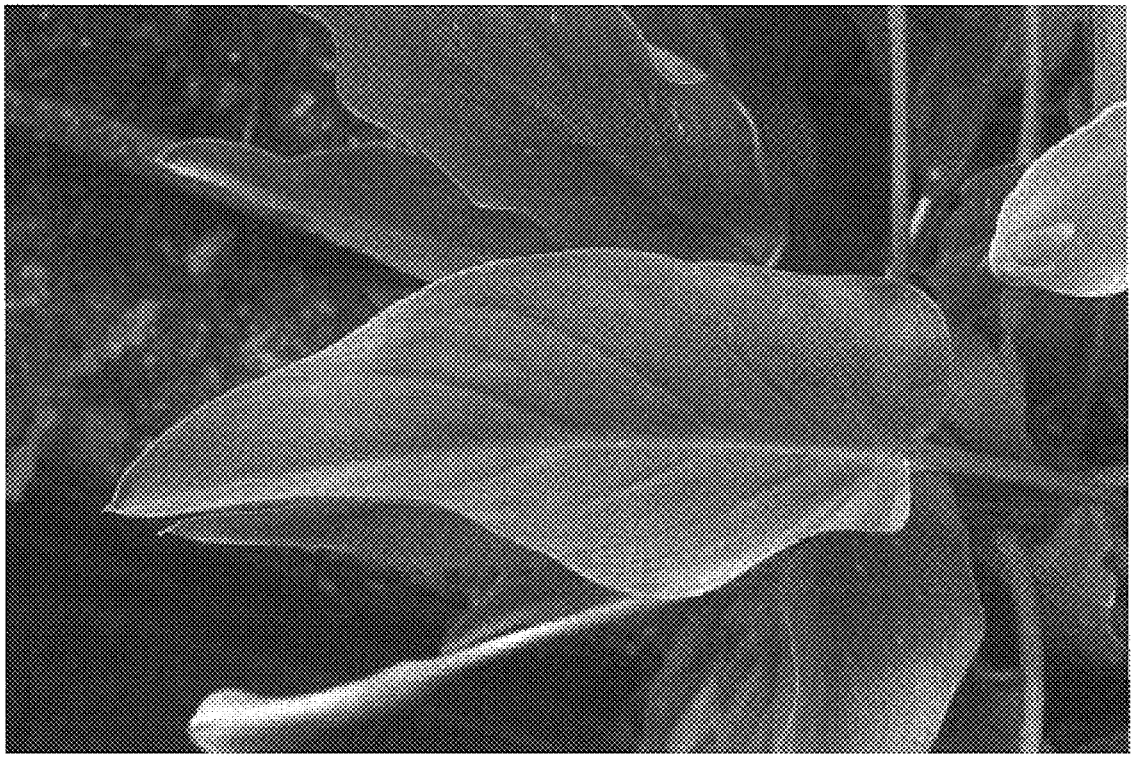
FIG. 3 is a close-up photograph of a leaf of the new variety.

The following observations, measurements, and comparisons describe plants grown in New Zealand under conditions which approximate those generally used in horticulture practice. Plants described were 14 weeks from planting date of tuber. Color references are made to The R.H.S. Colour Chart of The Royal Horticultural Society of London, except where general color terms of ordinary significance are used.

THE PLANT

Size:
- *Height of the leaf canopy above the soil.*—300–700 mm; Average of 500 mm.
- *Height of top of flowers above the soil.*—300–700 mm; Average of 500 mm.
- *Diameter.*—300–550 mm; Average of 500 mm.
- *Form.*—Erect.

Number of inflorescences per tuber size:
- *Diameter of 3–4 cm.*—4–6 flowers.
- *Diameter of 4–5 cm.*—6–10 flowers.
- *Diameter of 5–6 cm.*—10–16 flowers.

Branches:
- *Character.*—Strong.
- *Color.*—147A.
- *Number.*—2–8 per plant.

Leaves:
- *Size.*—Width: 65–130 mm; Average of 110 mm. Length: 200–280 mm; Average of 240 mm.
- *Shape.*—Ovate to cordate; one-half of leaf is slightly smaller than the other half.
- *Number per plant.*—10–30.
- *Color.*—Upper surface: 147A to 147B. Lower surface: 147B, with 144B to 144C veination.
- *Spotting or mottling.*—Description: 20–30 maculations per leaf, ranging from 1 mm dots to 12 mm long×1 mm wide lines. Color: Transparent.
- *Margin.*—154B.
- *Veins.*—Configuration: Pinnate. Color: 144B to 144C.
- *Surface quality.*—Leathery.

Petiole:
- *Length.*—200–500 mm; Average of 250 mm.
- *Color.*—144D with striations of 144A.

Roots:
- *Color.*—White.
- *Branching.*—Moderate, average.

THE INFLORESCENCE

Spathe:
- *Size.*—Length: 65–90 mm; Average of 80 mm. Width: 40–60 mm; Average of 55 mm.

*Color.*—Inner surface: Base of spathe is 12D, intensifying to 12A to 12B at the edge and toward the apex of the spathe. The yellow color has an overlay of 45C that becomes more intense at the outer edge and toward the apex of the spathe. Outer surface: Overall color is 23B. Striations of 144B to 144C run from the top of the peduncle onto the spathe and change from 12D to a more intense 12B to 12C at the outer edge and toward the apex of the spathe. The yellow color has an overlay of 45D becoming more intensely colored at the outer edge and toward the apex of the spathe. One half of the spathe is more strongly colored than the other half of the spathe.

*Veins.*—Color: Transparent at the base of the spathe, changing to 45C to 45D toward the outer edges of the spathe. Configuration: Parallel.

*Shape.*—Overall: Cupped. Tip: Reflexed. Base: Cylindrical and widening distally.

Spadix:

*Size.*—Length: 30–45 mm; average of 40 mm. Diameter: 4–10 mm.

*Color.*—Male organs: 7B, with specks of 45D. Female organs: 14A, with specks of 45D.

*Position relative to spathe.*—Upright.

Peduncle:

*Size.*—Length: 250–500 mm; Average of 420 mm. Diameter: 6–10 mm.

*Color.*—149D with striations of 144B to 144C; slightly mottled at the base.

Reproductive organs:

*Location of female organs.*—Basal position of the spadix (lower 40%).

*Location of male organs.*—Upper position of the spadix (upper 60%).

*Perianth.*—Conspicuous.

*Stamens.*—Visible before pollen release.

*Number per spadix.*—Between 12 to 25.

*Pistil.*—Length beyond perianth: 0.5 mm. Shape: Dome.

Flowering: Tubers planted in New Zealand begin to produce flowers 85 days after planting and continue to flower over a 20–30 day period.

Lastingness: Cut inflorescence last 5–14 days.

Fragrance: None.

Disease resistance: High.

Pest resistance: Moderate.

I claim:

1. A new and distinct variety of calla lily plant named 'Tahiti' as described and illustrated.

* * * * *